(12) United States Patent
Dyer et al.

(10) Patent No.: US 9,818,188 B2
(45) Date of Patent: Nov. 14, 2017

(54) SYSTEM AND METHOD FOR CONNECTIVITY MAPPING

(71) Applicants: Kelly Noel Dyer, Toronto (CA); Ali Raza Khan, London (CA)

(72) Inventors: Kelly Noel Dyer, Toronto (CA); Ali Raza Khan, London (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/501,914

(22) PCT Filed: Oct. 17, 2014

(86) PCT No.: PCT/CA2014/000740
§ 371 (c)(1),
(2) Date: Feb. 6, 2017

(87) PCT Pub. No.: WO2016/058075
PCT Pub. Date: Apr. 21, 2016

(65) Prior Publication Data
US 2017/0221208 A1    Aug. 3, 2017

(51) Int. Cl.
*G06K 9/34* (2006.01)
*G06T 7/00* (2017.01)
*G01R 33/56* (2006.01)
*G01R 33/563* (2006.01)
*G06T 7/11* (2017.01)

(52) U.S. Cl.
CPC ........ *G06T 7/0012* (2013.01); *G01R 33/5608* (2013.01); *G01R 33/56341* (2013.01); *G06T 7/11* (2017.01); *G06T 2207/10088* (2013.01)

(58) Field of Classification Search
None
See application file for complete search history.

(56) References Cited

U.S. PATENT DOCUMENTS 8,593,142 B2 * 11/2013 Mori ................ G01R 33/56341
324/309
2008/0188734 A1 * 8/2008 Suryanarayanan ..... G06T 7/149
600/407

(Continued)

OTHER PUBLICATIONS

Level set modeling and segmentation of diffusion tensor magnetic resonance imaging brain data, Leonid Zhukov et al., JOEI 12(1), Jan. 2003, pp. 125-133.*

(Continued)

*Primary Examiner* — Jayesh A Patel
(74) *Attorney, Agent, or Firm* — Perry + Currier Inc.

(57) ABSTRACT

A processing system for and a method of segmenting a physiological image is provided. Once the physiological image is received, extrinsic data defining extrinsic regions is further received. Additionally, intrinsic data defining at least one intrinsic region, each intrinsic region corresponding to one extrinsic region is received. A primary modification is performed, where a shape and size of at least one extrinsic region having a corresponding intrinsic region is modified based on a shape and size of the corresponding intrinsic region, to form a modified extrinsic data. The physiological image is segmented into segmented regions based on the modified extrinsic data, each segmented region which has a corresponding intrinsic region representing a primary modification based on the corresponding intrinsic region.

18 Claims, 3 Drawing Sheets

(56) References Cited

U.S. PATENT DOCUMENTS

| | | | | |
|---|---|---|---|---|
| 2009/0028403 A1* | 1/2009 | Bar-Aviv | ............. | G06F 19/321 382/128 |
| 2010/0322488 A1* | 12/2010 | Virtue | .................... | A61B 5/055 382/128 |
| 2013/0172727 A1* | 7/2013 | Mori | ..................... | A61B 5/055 600/407 |
| 2013/0223716 A1* | 8/2013 | Mori | ................... | A61B 5/0013 382/131 |

OTHER PUBLICATIONS

Zheng et al., "Fast Automatic Heart Chamber Segmentation from 3D CT Data Using Marginal Space Learning and Steerable Features" Physical Review A 64.1 (2001) "whole document".

Khan, A.R. et al., "Hybrid approach to automated fibre bundle extraction for neurosurgical planning", 2015 IEEE 12th International Symposium of Biomedical Imaging, IEEE Engineering in Medicine & Biology Society, Brooklyn, New York, Apr. 16-19, 2015, Unpublished conference paper. Western University, London, Ontario, 2015. Print.

Zheng et al., "Fast Automatic Heart Chamber Segmentation from 3D CT Data Using Marginal Space Learning and Steerable Features" Physical Review A 64.1 (2001).

Rohlfing et al., "Quo Vadis, Atlas-Based Segmentation?" in The Handbook of Medical Image Analysis—vol. III: Registration Models. New York: Kluwer Academic/Plenum, 2005, ch. 11, pp. 435-486.

Wu, Bill, International Search Report, PCT Application No. PCT/CA2014/000740 mailed Jun. 22, 2015.

Wu, Bill, International Preliminary Report on Patentability, PCT Application No. PCT/CA2014/000740 mailed Jan. 25, 2017.

* cited by examiner

SYSTEM AND METHOD FOR CONNECTIVITY MAPPING

FIELD OF THE INVENTION

The present invention relates generally to physiologic imaging. More specifically, the present invention relates to connectivity mapping in an acquired physiologic image.

BACKGROUND OF THE INVENTION

Magnetic resonance imaging (MRI) is a major imaging technique used in medicine. MRI is capable of generating detailed images of soft tissues such as the brain, muscles and kidneys. Specific properties of the various compounds found inside tissues, such as water and/or fat, are used to generate images. For example, when subjected to a strong magnetic field, the vector sum of the nuclear magnetic moments of a large number of atoms possessing a nuclear spin angular momentum, such as hydrogen, which is abundant in water and fat, will produce a net magnetic moment in alignment with the externally applied field. The resultant net magnetic moment can furthermore process with a well-defined frequency that is proportional to the applied magnetic field. After excitation by radio frequency pulses, the net magnetization thus allows a detectable signal to be generated.

The acquired signals form the basis from which images of the tissue being scanned is obtained. These images are typically a representation of the anatomy of the tissue being scanned. Moreover, the images obtained can be further enhanced by segmenting the anatomy into regions of interest. Segmentation into regions of interest is typically accomplished by mapping generic atlas data previously obtained from one or more different tissue samples, or based on the experience of experts in the field. However, the data obtained in this manner is not necessarily representative of the tissue at hand. Accordingly, there is a need to accurately enhance anatomical images based on regions of interest.

SUMMARY OF THE INVENTION

It is an object to provide a novel system and method for an MRI scanning system and method that obviates and mitigates at least one of the above-identified disadvantages of the prior art.

According to an aspect, a computer implemented method of segmenting a physiological image is provided. The method can comprise receiving extrinsic data defining extrinsic regions. Intrinsic data defining at least one intrinsic region can also be received. Each intrinsic region can correspond to one extrinsic region. As a primary modification, a shape and size of at least one extrinsic region having a corresponding intrinsic region can be modified based on a shape and size of the corresponding intrinsic region, to form a modified extrinsic data. The physiological image can be segmented into segmented regions based on the modified extrinsic data. Each segmented region which has a corresponding intrinsic region can represent a primary modification based on the corresponding intrinsic region.

The method can further comprise receiving intrinsic tract data comprising tracts. Waypoint regions can also be received and an identified bundle comprising an identified subset of the tracts can be identified based on the waypoint regions. The waypoint regions can include at least one endpoint region and the bundle can be identified based on the tracts that end at the at least one endpoint region. The waypoint regions can also include at least one pass-through region and the bundle can be identified based on the tracts that pass through the at least one pass-through region.

According to another aspect, a data processing system is provided. The data processing system can receive a physiological image, extrinsic data defining extrinsic regions and intrinsic data defining at least one intrinsic region. Each intrinsic region can correspond to one extrinsic region. As a primary modification, a shape and size of at least one extrinsic region having a corresponding intrinsic region can be modified based on a shape and size of the corresponding intrinsic region, to form a modified extrinsic data. The physiological image can be segmented into segmented regions based on the modified extrinsic data. Each segmented region which has a corresponding intrinsic region can represent a primary modification based on the corresponding intrinsic region.

These, together with other aspects and advantages which will be subsequently apparent, reside in the details of construction and operation as more fully hereinafter described and claimed, reference being had to the accompanying drawings forming a part hereof, wherein like numerals refer to like parts throughout.

DETAILED DESCRIPTION

Traditional magnetic resonance imaging (MRI) systems represent an imaging modality which is primarily used to construct pictures of magnetic resonance (MR) signals from protons such as hydrogen atoms in an object. In medical MRI, typical signals of interest are MR signals from water and fat, the major hydrogen containing components of tissues.

Figure 1:
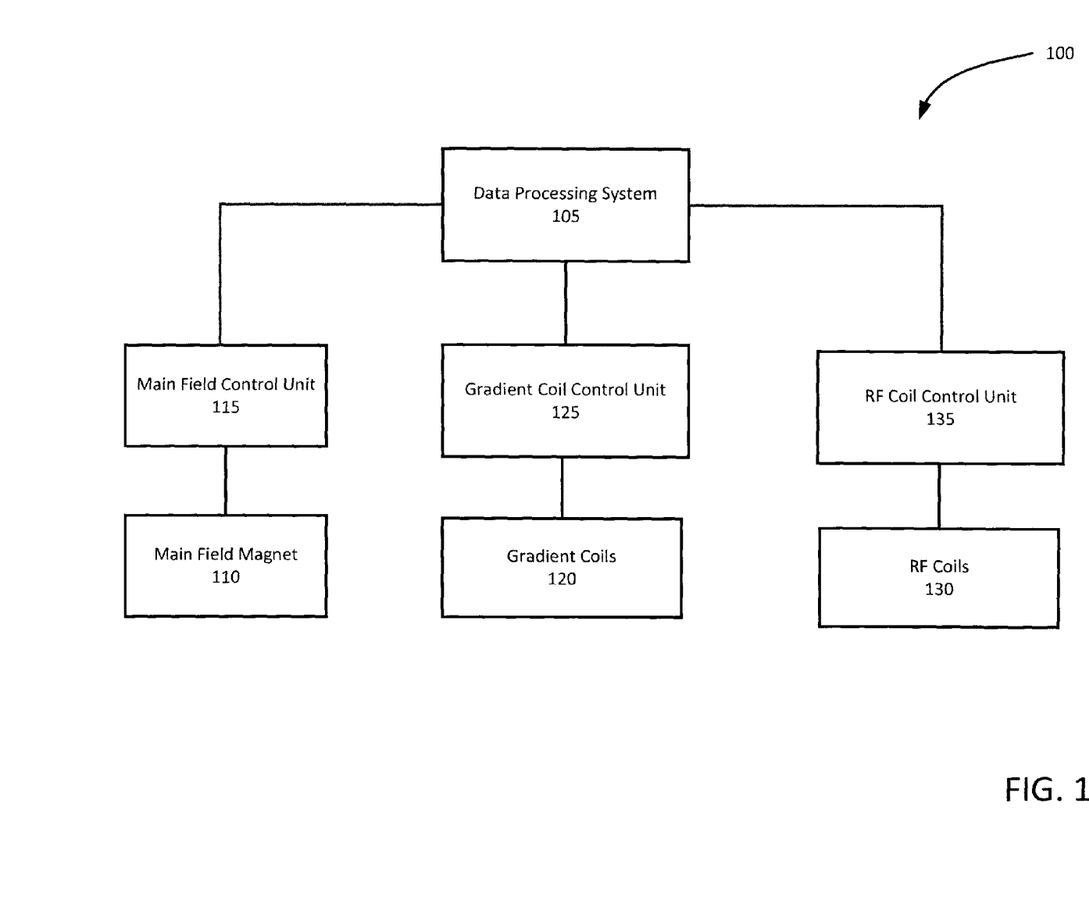
FIG. 1 shows a block diagram of functional subsystems of a magnetic resonance imaging (MRI) system in accordance with an implementation.

Referring to FIG. 1, a block diagram of a magnetic resonance imaging (MRI) system, in accordance with an example implementation, is shown at 100. The example implementation of MRI system indicated at 100 is for illustrative purposes only, and variations including additional, fewer and/or varied components are possible.

Figure 2:
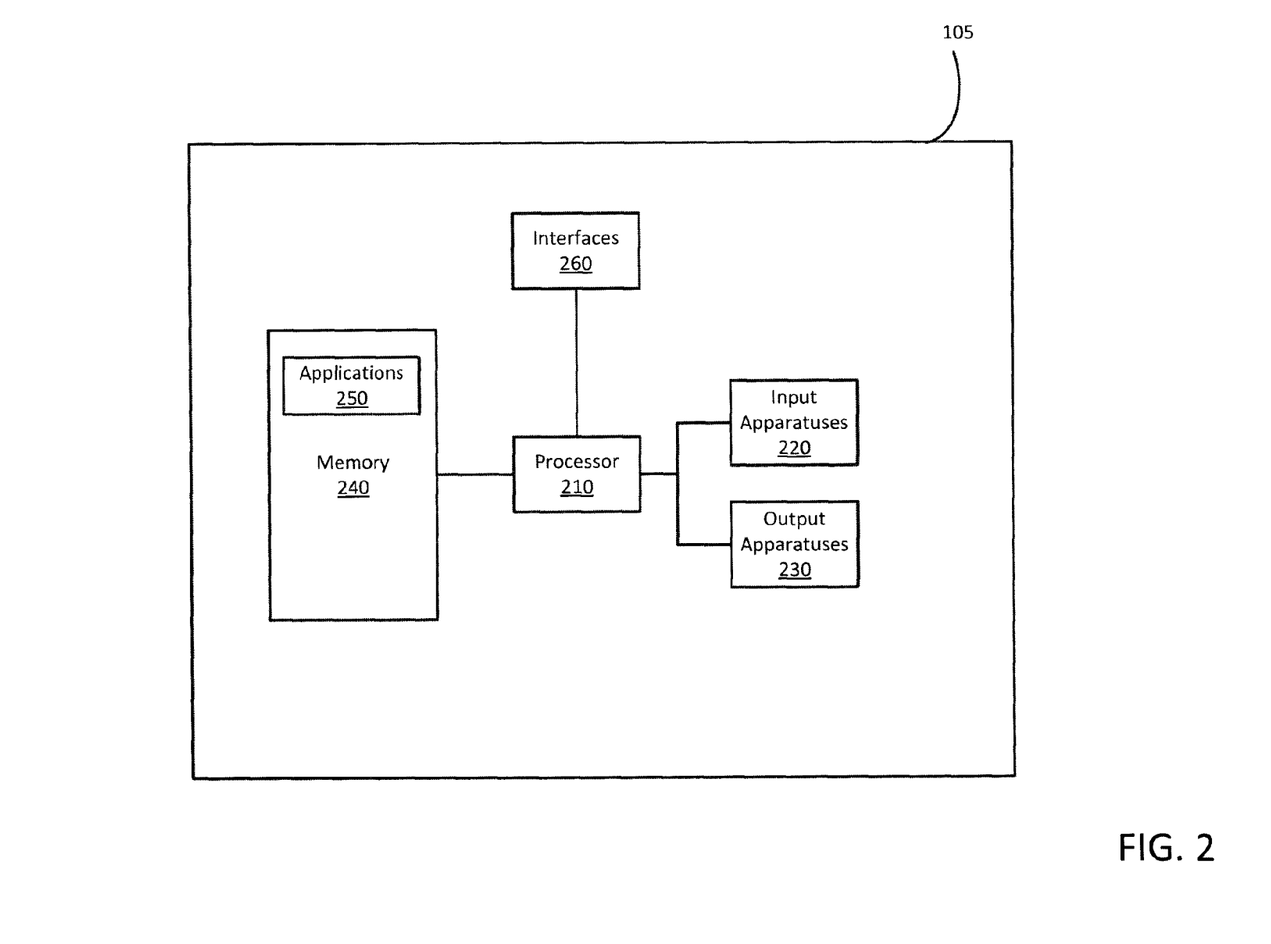
FIG. 2 shows a block diagram representation of an example data processing system in accordance with an implementation.

As shown in FIG. 1, the illustrative MRI system 100 comprises a data processing system 105. Referring to FIG. 2, an example computing system that can be part of the data processing system 105 responsible for image and data processing is shown. The data processing system 105 comprises a processor 210, one or more optional input apparatuses 220, output apparatuses 230 and memory 240. The processor 210 runs or executes operating instructions or applications 250 that are stored in the memory 240 to perform various functions for the data processing system 105. The processor 210 includes one or more microprocessors, microcontrollers, digital signal processors (DSP), state machines, logic circuitry, or any device or devices that process information based on operational or programming instructions or applications 250 stored in the memory 240. In accordance with the embodiments, the processor 210 processes various functions and data associated with carrying out image acquisition and processing.

The input apparatuses 220 are any apparatuses which allow the MRI system 100 to receive input from an operator. For example, the input apparatuses 220 may be a keyboard, a touch pad, a touch component of a display, a microphone, sensors for detecting gestures, buttons, switches or other apparatuses which may be used to receive operator input. In variations, combinations of such apparatuses may be used.

The output apparatuses 230 are any apparatuses capable of providing feedback to an operator. Accordingly, the output apparatuses 230 may be in the form of, for example, an audio apparatus, such as a speaker, a haptic device such as a vibrator, or a visual apparatus such as a display or a light emitting diode (LED), or a combination of such apparatuses.

The memory 240 is any apparatus or non-transitory medium capable of storing digital information. Accordingly, the memory 240 can include an IC (integrated circuit) memory chip containing any form of RAM (random-access memory) or ROM (read-only memory), a CD-RW (compact disk with read write), a hard disk drive, a DVD-RW (digital versatile disc with read write), a flash memory card, external subscriber identity module (SIM) card or any other non-transitory medium for storing digital information. The memory 240 maintains applications 250. The applications 250 include various software and/or firmware programs necessary for the operation of the MRI system 100 (e.g. image acquisition, data processing, etc.) that address specific requirements of the operator.

The data processing system 105 can further comprise one or more interfaces 260 adapted for communication and data exchange with the control units and the hardware components of the MRI system 100 for performing a scan.

Continuing with FIG. 1, the example MRI system 100 also includes a main field magnet 110. The main field magnet 110 can be implemented as a permanent, superconducting or a resistive magnet, for example. Other magnet types, including hybrid magnets suitable for use in the MRI system 100 will now occur to a person of skill and are contemplated. The main field magnet 110 is operable to produce a substantially uniform main magnetic field having a strength B0 and a direction along an axis. The main magnetic field is used to create an imaging volume within which desired atomic nuclei, such as the protons in Hydrogen within water and fat, of an object are magnetically aligned in preparation for a scan. In some implementations, as in this example implementation, a main field control unit 115 in communication with the data processing system 105 can be used for controlling the operation of the main field magnet 110.

The MRI system 100 further includes gradient coils 120 used for encoding spatial information in the main magnetic field along, for example, three perpendicular gradient axis. The size and configuration of the gradient coils 120 can be such that they produce a controlled and uniform linear gradient. For example, three paired orthogonal current-carrying primary coils located within the main field magnet 110 can be designed to produce desired linear-gradient magnetic fields.

In some implementations, the gradient coils 120 may be shielded and include an outer layer of shield coils which can produce a counter magnetic field to counter the gradient magnetic field produced by the primary gradient coils forming a primary-shield coils pair. In such a coil pair the "primary" coils can be responsible for creating the gradient field and the "shield" coils can be responsible for reducing the stray field of the primary coil outside a certain volume such as an imaging volume. The primary and shield coils of the gradient coils 120 may be connected in series. It is also possible to have more than two layers of coils for any given gradient axis that together form a shielded gradient coil. Shielded gradient coils 120 may reduce eddy currents and other interference which can cause artefacts in the scanned images. Since eddy currents mainly flow in conducting components of the MRI system 100 that are caused by magnetic fields outside of the imaging volume (fringe fields), reducing the fringe fields produced by the gradient coils 120 may reduce interference. Accordingly, the shapes and sizes, conductor wire patterns and sizes, and current amplitudes and patterns of the primary-shield coils pair can be selected so that the net magnetic field outside the gradient coils 120 is as close to zero as possible. For cylindrical magnets, for example, the two coils can be arranged in the form of concentric cylinders whereas for vertical field magnets, the two coils may be arranged in coaxial disks.

The conductive components of the gradient coils 120, whether shielded or unshielded and including the primary and shield coils, may consist of an electrical conductor (for example copper, aluminum, etc.). The internal electrical connections can be such that when a voltage difference is applied to the terminals of the gradient coils 120, electric current can flow in the desired path. The conductive components for the three gradient axes for both the primary gradient coils and the gradient shield coils can be insulated by physical separation and/or a non-conductive barrier.

The magnetic fields produced by the gradient coils 120, in combination and/or sequentially, can be superimposed on the main magnetic field such that selective spatial excitation of objects within the imaging volume occurs. In addition to allowing spatial excitation, the gradient coils 120 may attach spatially specific frequency and phase information to the atomic nuclei placed within the imaging volume, allowing the resultant MR signal to be reconstructed into a useful image. A gradient coil control unit 125 in communication with the data processing system 105 is used to control the operation of the gradient coils 120.

In some implementations of the MRI system 100, there may be additional electromagnet coils present (not shown), such as shim coils (traditionally, but not limited to, producing magnetic field profiles of 2nd order or higher spherical harmonics) or a uniform field offset coil or any other corrective electromagnet. To perform active shimming (correcting the field distortions that are introduced when different objects are placed within or around the system), the corrective electromagnets, such as the shim coils, carry a current that is used to provide magnetic fields that act to make the main magnetic field more uniform. For example, the fields produced by these coils may aid in the correction of inhomogeneities in the main magnetic field due to imperfections in the main magnet 110, or to the presence of external ferromagnetic objects, or due to susceptibility differences of materials within the imaging region, or any other static or time-varying phenomena.

The MRI system 100 further comprises radio frequency (RF) coils 130. The RF coils 130 are used to establish an RF magnetic field with a strength B1 to excite the atomic nuclei or "spins". The RF coils 130 can also detect signals emitted from the "relaxing" spins within the object being imaged. Accordingly, the RF coils 130 can be in the form of separate transmit and receive coils or a combined transmit and receive coil with a switching mechanism for switching between transmit and receive modes.

The RF coils 130 can be implemented as surface coils, which are typically receive only coils and/or volume coils which can be receive and transmit coils. The RF coils 130 can be integrated in the main field magnet 110 bore. Alternatively, the RF coils 130 can be implemented in closer proximity to the object to be scanned, such as a head, and can take a shape that approximates the shape of the object, such as a close-fitting helmet. An RF coil control unit 135 in communication with the data processing system 105 can be used to control the operation of the RF coils 130.

There are many techniques for acquiring images using the MRI system 100, including T1 and T2 weighted images. To provide a simplified illustration of the MRI system 100's functionality, simplified operations for obtaining proton density-weighted images are described as a non-limiting example. To create an image in accordance with the example illustration, the MRI system 100 detects the presence of atomic nuclei containing spin angular momentum in an object, such as those of Hydrogen protons in water or fat found in tissues, by subjecting the object to a relatively large magnetic field. In this example implementation, the main magnetic field has a strength of B0 and the atomic nuclei containing spin angular momentum may be Hydrogen protons. The main magnetic field partially polarizes the Hydrogen protons in the object placed in the imaging volume of the main magnet 110. The protons are then excited with appropriately tuned RF radiation, forming an RF magnetic field with a strength of B1, for example. Finally, weak RF radiation signal from the excited protons is detected as an MR signal, as the protons "relax" from the magnetic interaction. The frequency of the detected MR signal is proportional to the magnetic field to which they are subjected.

Cross-sections of the object from which to obtain signals may be selected by producing a magnetic field gradient across the object so that magnetic field values of the main magnetic field can be varied along various locations in the object. Given that the signal frequency is proportional to the varied magnetic field created, the variations allow assigning a particular signal frequency and phase to a location in the object. Accordingly, sufficient information can be found in the obtained MR signals to construct an anatomical map of the object in terms of proton presence, which is the basis of a traditional MRI image. For example, since proton density varies with the type of tissue, tissue variations may be mapped as image contrast variations after the obtained signals are processed.

In variations, an acquired image may be obtained using various other imaging systems and methods. For example, in some variations, anatomical images may be obtained using computed tomography (CT) scans. Anatomical images obtained with CT scans are more sensitive to denser tissues such as bones, and thus can be more appropriate for use in cases where the tissue of interest is a denser tissue. However, CT scans may also be used for soft tissue imaging, where MRI systems are not available for example. Other methods of obtaining acquired images will now occur to a person of skill and are within scope.

The acquired images may be two or three dimensional. For example, a typical MRI image is a two dimensional volumetric slice through the tissue being scanned. The gradient coils 120 allow the selection of a particular slice of the tissue to be scanned. Similarly, a typical CT image is a two dimensional slice obtained based on X-Ray imaging techniques. Two dimensional images obtained through MRI or CT scans may be combined, through various image processing techniques to form three dimensional images, representing a volume of tissue that is of interest, such as the brain or a portion of the brain. Other imaging techniques allow obtaining images that have different dimensionality. For example, electroencephalograph EEG based images are typically images that represent electrical activity along the surface of the brain up to a certain depth.

Once an acquired image representing a subject, such as a tissue of interest, is obtained, the acquired image can be enhanced through the use of data that allows a regional segmentation of the acquired image. For example, in some implementations, the acquired images can be segmented to show different regions of interest.

Regions of interest can be defined based on various considerations. For example, the regions can be defined on the basis of anatomic substructures. A brain image, for example, can be segmented to identify the hippocampus, the cerebellum and the ventricles, amongst others. Alternatively, a lung image can be segmented to indicate alveoli, and bronchi. In other implementations, the regions can be identified based on tissue function. For example, for the brain, image regions can identify the primary visual area, the motor area and the primary auditory area, amongst others.

Data defining regions of interest can be obtained from various sources. Functional MRI (fMRI) images are one such source. For example, fMRI images can be source data for defining functional areas of the brain. The choice of specific pulse sequences with optimized parameters can be used by the MRI system 100 to exploit tissue contrast to obtain images that are able to depict different characteristics of tissue and materials. For example, T2* relaxation has a significant contribution on relative signal intensities immediately following a 90° RF pulse. T2* relaxation can be one of the main determinants of image contrast with GRE pulse sequences and forms the basis for many magnetic resonance (MR) applications, including fMRI.

fMRI studies rely on regional differences in cerebral blood flow to delineate regional activity. Blood Oxygenation Level Dependent Imaging (BOLD) is a technique used to generate images in function MRI studies. BOLD-fMRI is able to detect differences in cerebral blood flow in part due to a difference in the paramagnetic properties of oxygenated hemoglobin and deoxygenated hemoglobin. Deoxygenated hemoglobin can be more strongly paramagnetic than oxygenated hemoglobin, and therefore the former can cause greater local dephasing of protons. The local dephasing can reduce the MR signal from the tissues in its immediate vicinity. T2* weighted pulse sequences can be used to detect this change. Accordingly, by subjecting a patient to appropriate tasks while fMRI images are acquired, the regions of brain associated with the functions required to perform the task can be identified based on oxygenation differences in the tissues being scanned.

An alternative source of data that can be used for defining regions of interest in an acquired image is magnetic resonance (MR) diffusion tractography. For example, tractography images can be the basis for identifying white matter substructures in the brain. Neuronal tracts or connections connecting different regions of the brain and forming, at least in part, the white matter of the brain, can be identified based on tractography images. White matter typically consists of bundles of myelinated axons. Diffusion coefficients for white matter are generally lower in comparison with water. Moreover, diffusion coefficients are lower across the diameter of the tracts as opposed to along the length of the tracts. Hence, by measuring diffusion along many directions and observing that it is faster in one direction than in others, the orientation of the tracts can be measured. Once the direction of the tracts are measured, they can be joined up to reconstruct entire pathways.

In its simplest form, detecting tracts may be performed using deterministic tractography. Accordingly, the methodology consists of performing a direction measurement at an initial (seed) location and continuing to take measurements along the measured direction until a new direction is detected. The measurements subsequently follow this new direction and carry on until the entire pathway is traced.

White matter tracts typically have diameters on the order of 1 micrometer (μm), but each measurement is performed (e.g. at each voxel of the image) is at the scale of approximately 2-3 millimeters (mm). Typically, however, connections between different regions of the brain are organized into large tracts containing hundreds of thousands of axons that are largely coherently organized. Accordingly, voxels can provide sufficient resolution to identify such tracts. In variations other, more sophisticated tractography techniques can be used to detect tracts. In further variations, tractography can be performed as whole brain tractography or specific bundle tractography. In whole brain tractography, the whole brain is used as a seed, in specific bundle tractography regions of interest are used as seeds.

In some implementations, once tracts are detected, they may be further segmented into substructures or functional areas such as bundles. The segmentation can be performed based on additional data and/or manual input, as well as the acquired image which may itself be segmented on the basis of the tracts. For example, the bundles can be identified based on waypoints. Accordingly, the segmented regions of an acquired image can include regions defined as discrete anatomical or functional waypoints that indicate anatomical or functional structures where white matter bundles may begin, pass-through, or terminate. As an example, bundles can be defined based on the functional end-point regions they connect, such as the optic radiation bundle, which connects the visual cortex endpoint region with the lateral geniculate nucleus endpoint region of the thalamus. As another example, bundles can be defined by the anatomical end-point regions they connect, such as the inferior longitudinal fasciculus bundle that connects the temporal pole endpoint and the occipital pole endpoint region in each hemisphere of the brain. Other bundles may be defined by the anatomical location of their pathways, such as the callosal fibers, which connect the two hemispheres through the corpus callosum. Yet other bundles can be identified based on pass-through regions, regions through which the bundles pass. In some variations, some regions can be identified as exclusion regions. Tracts passing through or connecting such exclusion regions can be excluded from the identified bundles.

In further variations, data from multiple sources may be combined to identify different regions of interest. For example, in one variation, fMRI images can be used to identify functional areas of an acquired image of a brain. Moreover, tractography data can be used to identify bundles in the white matter of the acquired image. Accordingly, the acquired image representing the subject (the scanned brain) can be segmented based on the functional areas and the bundles defined by the data sources. The segmented anatomical image can allow the visualization of how each functional area is connected to other functional areas. In a further variation, additional data may be obtained that allows the visualization of different brain structures such as the hippocampus, and thus allowing the relationship between functional areas and anatomical substructures, as well as their connectivity through bundles to be visualized.

In some implementations, data, based on which regions of interest can be identified in an acquired image, can be classified as intrinsic and extrinsic. Specifically, extrinsic data include data which is obtained from sources other than the subject being scanned for the acquired image. For example, in some variations, extrinsic data can include atlas data. Atlas data can be based on a single subject's anatomy, but is more typically obtained from multiple sources such as different tissue samples or patients. The data obtained from multiple sources is correlated and combined using various image and data processing techniques to align the anatomy of multiple subjects together. Accordingly, regions in an atlas are typically averages for a population. Atlas data may also be generated manually. For example, an atlas can be created by receiving data representative of the regions through an input mechanism. The input mechanism may, for example, be a mouse, a digital pen, or other similar input mechanism which would allow a user to, for example, digitally input and manipulate the regions. Atlas data can also be transferred from one atlas to another using various image and data processing techniques to align the anatomy of the atlases.

Because extrinsic data can be obtained independently of the subject being imaged, sufficient time is typically available to generate extrinsic data, such as atlas data, which defines all or most of the regions in a given tissue. For example, atlas data defining all or most of the functional areas of a brain can be available.

Intrinsic data, on the other hand, is typically obtained, directly or indirectly, from the subject from which the anatomical image is obtained. For example, various automatic, manual or assisted image processing techniques may be used to define functional areas or substructures such as the hippocampus from the anatomical images of the subject. Alternatively, or in addition, further images and data may be obtained from the subject tissue or patient based on which one or more regions may be defined. The additional images may be obtained may be MRI images such as fMRI images or images and data based on other imaging and data acquisition modalities such as CT scans and EEG.

Since intrinsic data is obtained from the subject, generally time is of the essence. For example, intrinsic data may be obtained in preparation for surgery or during surgery itself. Accordingly, resources and time are rarely sufficient to obtain intrinsic data that defines all or most of the regions for a given subject. Instead, typically, one or more regions are selected as important or relevant, based for example on where surgical incisions can occur, and intrinsic data can be obtained to define those selected regions. Accordingly, typically, the number of regions that can be defined on the basis of intrinsic data is fewer than the number of regions that can be defined on the basis of extrinsic data.

One of the key advantages of using intrinsic data is that intrinsic data can often indicate any anomalies associated with a specific subject that would not be detectable based on extrinsic data. For example, in the brain, the size of functional areas can vary greatly. As an example, regions associated with fine finger control may be much larger, in comparison to the average population, when the subject is a professional pianist. Alternatively, when the subject is blind, the areas typically associated with vision can acquire functionality other than sight. Such acquired functionality cannot generally be accurately identified from extrinsic data.

In further variations, a subject may have an additional mass which is not typically found in the general population. For example, a cyst or a tumor may be present in the brain. Such additional masses typically cause distortions in the surrounding tissues, thus significantly altering the regional makeup of the subject's tissue in comparison to others in the general population. Accordingly, obtaining intrinsic data in the areas surrounding the additional mass may be crucial for accurately identifying regions of interest in the subject's anatomical image.

Extrinsic data can be aligned to the acquired image, for example by obtaining the spatial warp that brings the associated extrinsic images in close alignment with the acquired image. This warp can be coarse, consisting of global translation, rotation, stretching, compression, and shearing, or can be fine, consisting of local deformation of the image.

In some variations, intrinsic data may be used to adjust extrinsic data. For example, intrinsic data may be obtained that corresponds to at least some of the extrinsic data. Accordingly, portions of the extrinsic data corresponding to the intrinsic data may be modified to align with the intrinsic data. As an example, an atlas of functional areas may be received, as well as intrinsic data defining the motor area. The atlas data related to the motor area can be altered to correspond to that defined by the intrinsic data. For example, the atlas data may be altered such that the motor area defined matches, in size and shape, the area identified by the intrinsic data. Alternatively, the size and shape may be altered to fall in between that of the atlas data and the intrinsic data, as a result of a mid-way interpolation, for example. Other methods of varying the atlas data to achieve an improved correspondence to the intrinsic data will now occur to a person of skill and are contemplated.

In variations, intrinsic data may not be available for a complete region identified by extrinsic data. For example, continuing with the above example of the motor area, the intrinsic data may only define a portion of the motor area identified in the atlas. In such variations, different methods can be used to estimate the complete shape of the region based on the intrinsic data. The extrinsic data can then be modified to correspond to the estimated shape. Alternatively, the extrinsic data could be modified only for the portions of the region that are defined by the intrinsic data.

In further variations, once a region, or a portion of a region defined by the extrinsic data is modified as a primary modification, based on intrinsic data, the remaining regions defined by the extrinsic data may also be adjusted, as a secondary modification, in accordance with the primary modifications done to the modified region. For example, continuing with the above example, the intrinsic data may indicate significant compression of the motor cortex due to a tumor. Once the atlas area for the motor cortex is adjusted to reflect the compression as a primary modification, the areas adjacent to the motor cortex may also be adjusted, as a secondary modification, to reflect any compression that may occur in those areas due to the tumor. The adjustment to the adjacent areas can be based on various predictive methods that can predict compression due to the compression of one area based on an additional mass not present in general population. Alternatively, in some variations the shape of an area defined by the atlas data can be modified, based on intrinsic data, the difference in shapes resulting from individual variations other than additional masses, such as plasticity based variations in the brain. In these variations, other predictive methods can account for changes to the shape of regions surrounding the area whose shape is modified based on the intrinsic data.

In additional variations, adjustments to the extrinsic data may be based on more than one intrinsic data set, obtained from one or more sources. For example, intrinsic data defining a motor area may be obtained based on fMRI images as well as EEG data. In some variations, one intrinsic data set may be used to verify another intrinsic data set. In other variations, the intrinsic data sets may be altered on the basis of each other. For example, when the shapes and/or sizes of the two intrinsic data sets are different, they may be averaged and the average may be used to adjust the extrinsic data.

In yet other variations, extrinsic data can be obtained from multiple sources. For example, extrinsic data defining functional areas may be obtained based on fMRI data as well as manually drawn data. In some variations, one extrinsic data set may be used to verify another extrinsic data set. In other variations, the extrinsic data sets may be altered on the basis of each other. For example, when the shapes and/or sizes of the regions defined by two extrinsic data sets are different, they may be averaged.

Images acquired by the MRI system 100, as well as intrinsic and extrinsic data may be processed, for example, combined, segmented or otherwise transformed, using the data processing system 105. The data processing system 105 may be any computing device capable of communicating with and processing data from the various control units and other hardware modules of the MRI system 100. The data processing system 105 can take form of, but is not limited to, a desktop, a laptop or notebook computer, a server and the like. Embodiments may be advantageously implemented to perform data and image processing using the MRI system 100.

In variations, image and data processing may be carried out at a data processing system or a computing system that is distinct and apart from the MRI system 100, such a desktop computer, a server, a laptop or any other computing system that is operable to perform image and data processing.

The acquired image of a subject, such as an image of the brain, may be processed to identify and segment multiple regions of interest. For example, an acquired image obtained using the MRI system 100 based on pulse sequences for generating proton density-weighted images may be segmented based on extrinsic and/or intrinsic data to indicate different regions in that image. As mentioned above, the regions can correspond to various areas such as different substructures and functional areas. The segmentation may be performed using various techniques. For example, if the data being based on which the acquired image is segmented, is in the form of images obtained using the same or similar mechanisms, such as proton density-weighted MRI images and data comprising functional MRI image, the data images and the acquired image may be registered using known mechanisms to properly align the images such that the regional information is aligned with the subject of the image. The registration may involve one or more transformations, such as rotation, translation, stretching, shrinking and others, of the one or both of the acquired image and the data images.

In variations, the data may be represented in a format different from the acquired image. For example, in some variations, an atlas may be in the form of geometric data providing the coordinates of regional boundaries. For these variations, appropriate methods can be used to map the data to the appropriate portions of the acquired image.

Once the regions are properly aligned with the anatomical image, the image can be segmented based on the regions defined by the data. The segmented regions can be represented at the acquired image using various methods such as color, shading, outlining, and others that will now occur to a person of skill. In variations, text labels or other symbols may also be used, alone or in combination with other methods of representing regions.

To further enhance the acquired image, tract data may be obtained from the subject, on the basis of diffusion imaging as discussed above, forming additional intrinsic data. In variations, tract data may be obtained as extrinsic data, based on tract atlases. The tract data can be registered and mapped to the acquired image, enabling the visualization of tract information.

Tract data can be segmented, based on selected ones of the identified regions of interest, to identify bundles and thus provide bundle location information. Knowledge bundle locations can be invaluable. For example, providing a surgeon an indication of which bundles would be damaged based on a planned surgical trajectory can afford an opportunity to alter the surgical trajectory to avoid more important bundles such as those involving connectivity of the primary visual area.

In variations where the modified extrinsic data is not sufficiently modified to account for individual variability, the resulting bundles can include tracts that are not a member of the specified bundle (false positives), or they may fail to include tracts that are indeed a member of the specified bundle (false negatives). Accordingly, such bundles may be resegmented so as to reflect their interfaces in the acquired image, by manually correcting the waypoints or exclusion regions that define the bundle.

In further variations, where the tract data is obtained as intrinsic data from the subject from whom the acquired image is obtained, the tract data may have deficiencies. For example, there may be cases where the acquired diffusion images contain regions of decreased directionality information, such as those caused by edema related to a tumour. In these cases, waypoints that define the pathway of an anatomical bundle that courses through these regions may fail to provide sufficient information to extract bundles and lead to a large degree of false negatives because of the interrupted pathways. To alleviate this, an additional or alternative form of bundle identification can be used that does not rely on definition of waypoints, but rather on the overlap of a tract's spatial coordinates with an extrinsic bundle atlas. The extrinsic bundle atlas may comprise probability representation of bundles or may comprise spatial tract data obtained from additional modalities such as fMRI.

In accordance with this alternative method, the extrinsic bundle atlas can be registered with and mapped to the tract data. A bundle can be selected from the extrinsic bundle atlas. The tracts in the intrinsic tract data whose spatial coordinates overlap, at least in portion, with the identified bundles can then be identified as belonging to the selected bundle. The portion may be predefined and based on a portion of length for example. In variations, the bundles can be identified based on selected waypoints, and the tracts identified based on overlap with the extrinsic bundle atlas can be added to those identified from the tract data based on the waypoint-based tract selection.

The aforementioned methods of bundle segmentation results in a set of tracts for each bundle, and thus a given tract may belong to one or many bundles. In some variations, the tract data may be further processed to associate each tract with a single bundle. Accordingly, first, representative tract can be identified for each anatomical bundle. For example, the average representation may be an average spatial midpoint for each bundle. This representative tract can be identified by averaging all the longitudinal tract locations within the bundle or by choosing the tract which has minimal spatial distance to all other tracts in the bundle. For example, the representative tract for a cylindrical bundle can be the tract running along the longitudinal axis of the cylinder. In some variations, especially for complex bundles, multiple tracts may be used to represent a single bundle.

Second, all tracts in the received tract data, over the whole brain, can be compared against each representative tract to determine a distance between each tract and the representative tract. The determination can be based on a suitable distance metric, such as the mean closest point distance or the maximum closest point distance (also known as the Hausdorff distance).

Third, each tract's bundle association can be determined based on the determined distances. Thus, each tract can be associated the bundle whose representative tract it is closet to, as long as that distance is below a specified threshold. Tracts which are farther away than the threshold distance from all representative tracts are labelled as unclassified. In some variations, the threshold can be varied to visualize bundles in the brain with a varying level of confidence. In further variations, the bundle labels may be defined hierarchically, such that tracts can belong to multiple bundles, where one bundle can be defined as a sub-bundle of another.

In variations, extrinsic tract data can also be modified on the basis of the adjustments made to other extrinsic and intrinsic data, in this example the modified extrinsic functional area atlas data. For example, tract data intersects functional areas identified in the atlas data. Those tracts that intersect the adjusted portions of the atlas data may thus be adjusted themselves so that the intersections continue to occur in an appropriate manner, for example, preventing intersections with a tumor.

Figure 3:
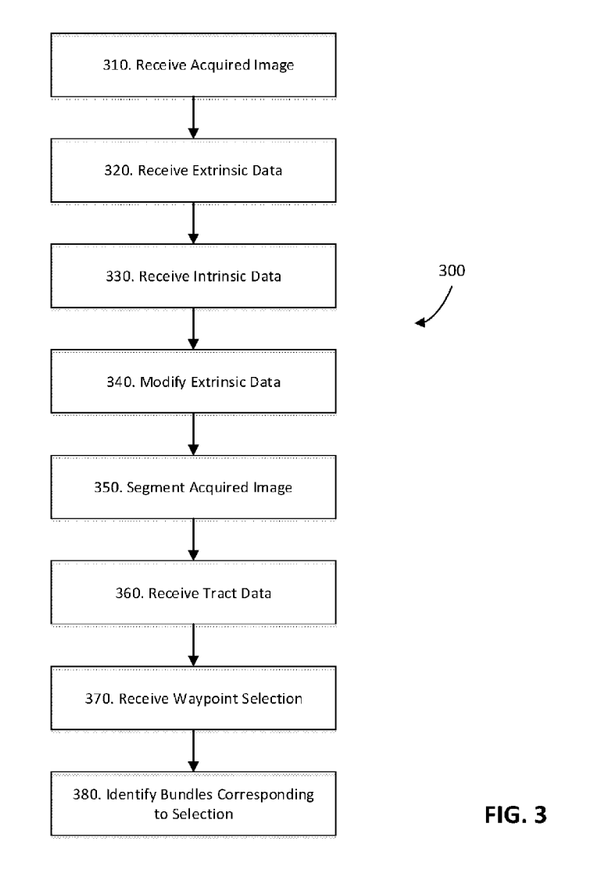
FIG. 3 shows method of image segmentation using the MRI system of FIG. 1 in accordance with an embodiment.

Referring now to FIG. 3, a method of medical image segmentation based on intrinsic and extrinsic data is indicated generally at 300. In order to assist in the explanation of the method, it'll be assumed that method 300 is in part operated using the MRI system 100 as shown in FIG. 1. Additionally, the following discussion of method 300 leads to further understanding of system 100. However, it is to be understood that system 100, and method 300 can be varied, and need not work exactly as discussed herein in conjunction with each other, and that such variations are within scope.

Starting at 310, an acquired image is received. In this example, the image is a three dimensional MRI image of the brain obtained from a series of sectional images obtained. Specifically, each sectional image is using the MRI system 100 based on pulse sequences for generating T1-weighted images.

Continuing with method 300, at 320 extrinsic data is received corresponding to functional areas of the brain. The functional areas defined include an area corresponding to the primary visual area. In this example, the atlas information is understood to be obtained from sources other than the subject for which the acquired image was obtained at 310. For example, the atlas may be obtained from multiple previously obtained scans from different patients which were combined and manually segmented to define the functional areas. Accordingly, in this example, the extrinsic data can be in the same format as the MRI.

Referring back to FIG. 3, intrinsic data is received at 330. In this example, one type of intrinsic data comprises fMRI images, which can be processed to identify the primary visual cortex. In some variations, intrinsic data comprises a segmentation of a tumour or lesion, obtained manually or through a computer-assisted method. Variations may include a segmentation of sub-parts of the lesion, such as infiltrative components, cystic components, or necrotic components.

Further variations could include anatomical landmarks identified on the acquired images, such as the anterior commissure.

Continuing with the method 300, at 340, the extrinsic data can be modified on the basis of the intrinsic data. To perform the modification, the anatomical images relating to the extrinsic data and the intrinsic data can be first coarsely aligned. Once the data sets are coarsely aligned, the regions in the extrinsic atlas data can be modified, or spatially warped, on the basis of the size, shape, location, and nature of the intrinsic data. In this example, the intrinsic data comprises the region obtained from fMRI that relates to the primary visual cortex. In another variation, where the intrinsic data comprises a segmentation of a tumour or lesion, the extrinsic data is modified based on the deforming properties of the segmented lesion, compressing nearby anatomy in the extrinsic atlas. In some variations, where sub-parts of the lesion are identified, the extrinsic data can be modified more specifically, for example, infiltrative components would not displace or compress the anatomical regions.

Continuing with FIG. 3, at 350 the acquired image is then segmented into regions based on the modified extrinsic data to enable visualization of different regions on the acquired image. To accomplish the segmentation, the modified extrinsic data can be registered and mapped to the acquired image obtained at 310. The acquired image can then be segmented and appropriate labels can be used to identify the segmented regions. Accordingly, the three dimensional acquired image obtained at 310 can be used to visualize various functional areas, and in variations anatomical areas and other regions of interest. Moreover, those functional areas that are considered to be important, are segmented, at least in part, based on intrinsic data which was used to modify the extrinsic data, and are thus known, with greater certainty, to be an accurate representation of the functional area for the subject from which the image was acquired.

Continuing with the method 300, at 360 tract data is obtained. Tract data can be obtained from the subject, on the basis of diffusion imaging as discussed above, forming intrinsic data. The tract data can be registered and mapped to the image obtained at 310, enabling the visualization of tract information.

To identify bundles based on tract data, one or more waypoints are selected at 370. One or more of the segmented regions of the acquired image can be selected as waypoints. Alternatively, waypoints may be selected manually by manually identifying regions of the acquired image that do not correspond to the segmented regions of the acquired image.

In this example, a selected waypoint is a manually identified region of the acquired image which corresponds to a portion of the brain which will be cut to reach a tumor during a brain operation. This manually identified region within the acquired image does not correspond to one of the segmented regions and represents a pass-through region, a waypoint through which a bundle passes. Additionally selected waypoints correspond to endpoint regions of great importance, which in this case are the visual areas of the brain which are identified based on the segmented regions of the acquired image.

Next, at 380 the tract data is segmented to identify bundles corresponding to selected waypoints. Accordingly, in this example, the bundles to be extracted from the tract data are bundles connecting the visual areas of the brain that pass through the region of the operation to be performed. Tracts that pass though the identified pass-through point, but do not belong to the specific anatomical bundle as defined by the selected endpoints can be removed. The segmentation can, accordingly, be performed by selecting tracts that pass through the set of pass-through points, identified manually from the acquired image and connect the selected segmented regions of the acquired image.

Although in the above example implementation of method 300 the extrinsic data is modified prior to segmenting the image, it is to be understood by persons of skill that the modification of extrinsic data and segmenting the image can happen in any order. For example, in variations, the image can be segmented based on the extrinsic data, and the segmentation modified on the basis of the intrinsic data.

The above-described embodiments are intended to be examples and alterations and modifications may be effected thereto, by those of skill in the art, without departing from the scope which is defined solely by the claims appended hereto. For example, methods, systems and embodiments discussed can be varied and combined, in full or in part.

We claim:

1. A computer implemented method of segmenting a physiological image comprising:
   receiving extrinsic data defining extrinsic regions;
   receiving intrinsic data defining at least one intrinsic region, each intrinsic region corresponding to one extrinsic region; and
   modifying a shape and size of at least one extrinsic region having a corresponding intrinsic region based on a shape and size of the corresponding intrinsic region, to form a modified extrinsic data;
   segmenting the physiological image into segmented regions based on the modified extrinsic data, each segmented region which has a corresponding intrinsic region representing a modification based on the corresponding intrinsic region;
   receiving intrinsic tract data comprising tracts;
   receiving waypoint regions;
   identifying a bundle comprising an identified subset of the tracts; and
   updating the modified extrinsic data with tract data indicative of said bundle.

2. The method of claim 1 further comprising:
   modifying a shape and size of at least one of the extrinsic regions, other than the at least one extrinsic region having a corresponding intrinsic region.

3. The method of claim 1 wherein the waypoint regions include at least one endpoint region and the bundle is identified based on the tracts that end at the at least one endpoint region.

4. The method of claim 1 wherein the waypoint regions include at least one pass-through region and the bundle is identified based on the tracts that pass through the at least one pass-through region.

5. The method of claim 1 further comprising:
   receiving an exclusion region; and excluding tracts associated with the exclusion region from the identified subset of the tracts.

6. The method of claim 1 wherein at least one waypoint region is selected from the segmented regions.

7. The method of claim 1 wherein at least one waypoint region is selected manually from the physiological image.

8. The method of claim 1 further comprising
   receiving an extrinsic bundle atlas including extrinsic bundles;
   identifying additional tracts based on the tracts and the extrinsic bundles;
   modifying the identified bundle to include the additional tracts.

9. The method of claim 8 further comprising:
receiving a selection of one of the extrinsic bundles,
wherein the identifying the additional tracts further comprises:
  determining that the additional tracts overlap, at least in part, with the selected extrinsic bundle.

10. The method of claim 1 further comprising:
identifying additional bundles based on the waypoint regions and the tracts;
identifying, for the identified bundle and each of the additional bundles, a corresponding representative tract;
determining, for each tract, a closest representative tract based on a distance to each of the representative tracts;
for each tract:
  when the closest representative tract is farther than a threshold, labelling the tract as unclassified; and
  when the closest representative tract is closer than said threshold, associating the tract with the bundle corresponding to the closest representative tract.

11. The method of claim 1 wherein the extrinsic data is obtained from at least two different sources.

12. The method of claim 1 wherein the intrinsic data is obtained from a first source and a second source different from the first source.

13. The method of claim 1 wherein the tract data is based on intrinsic magnetic resonance diffusion tractograpy.

14. The method of claim 12 wherein the intrinsic data from the second source is used to perform at least one of:
verify the intrinsic data obtained from the first source; and
modify the intrinsic data obtained from the first source.

15. A data processing system comprising:
a processor configured to:
  receive a physiologic image;
  receive extrinsic data defining extrinsic regions;
  receive intrinsic data defining at least one intrinsic region, each intrinsic region corresponding to one extrinsic region; and modify a shape and size of at least one extrinsic region having a corresponding intrinsic region based on a shape and size of the corresponding intrinsic region to from a modified extrinsic data; and
  segment the physiologic image into segmented regions based on the modified extrinsic data, each segmented region which has a corresponding intrinsic region representing a modification based on the corresponding intrinsic region;
wherein the processor is further configured to:
  receive intrinsic tract data comprising tracts;
  receive waypoint regions;
  identify a bundle comprising an identified subset of the tracts; and
  update the modified extrinsic data with tract data indicative of said bundle.

16. The data processing system of claim 15 wherein the processor is further operating to:
modify a shape and size of at least one of the extrinsic regions, other than the at least one extrinsic region having a corresponding intrinsic region.

17. The data processing system of claim 15 wherein the waypoint regions include at least one endpoint region and the identified bundle is identified based on the tracts that end at the at least one endpoint region.

18. The data processing system of claim 15 wherein the waypoint regions include at least one pass-through region and the identified bundle is identified based on the tracts that pass through the at least one pass-through region.

* * * * *